US008224456B2

(12) United States Patent
Daglow et al.

(10) Patent No.: US 8,224,456 B2
(45) Date of Patent: Jul. 17, 2012

(54) DIRECTIONAL STIMULATION LEAD AND ORIENTATION SYSTEM

(75) Inventors: Terry Daglow, Allen, TX (US); Brian Franz, Flower Mound, TX (US); John H. Erickson, Plano, TX (US); Sandy Hooper, Allen, TX (US); Tim Jones, Carrollton, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 2168 days.

(21) Appl. No.: 10/996,803

(22) Filed: Nov. 24, 2004

(65) Prior Publication Data
US 2005/0171587 A1     Aug. 4, 2005

Related U.S. Application Data

(60) Provisional application No. 60/524,982, filed on Nov. 25, 2003.

(51) Int. Cl.
*A61N 1/00* (2006.01)

(52) U.S. Cl. .......... 607/116; 607/61; 607/117; 607/118; 607/122

(58) Field of Classification Search ............... 607/61, 607/116–118, 122
See application file for complete search history.

(56) References Cited

U.S. PATENT DOCUMENTS

| | | | |
|---|---|---|---|
| 5,054,492 A | 10/1991 | Scribner et al. | 128/662.06 |
| 5,222,494 A * | 6/1993 | Baker et al. | 607/118 |
| 5,374,285 A * | 12/1994 | Vaiani et al. | 607/117 |
| 5,456,254 A | 10/1995 | Pietroski et al. | 128/642 |
| 5,645,580 A * | 7/1997 | Moaddeb et al. | 607/122 |
| 5,702,365 A * | 12/1997 | King | 604/105 |
| 5,735,887 A * | 4/1998 | Barreras et al. | 607/60 |
| 5,989,206 A * | 11/1999 | Prosl et al. | 604/5.01 |
| 6,216,045 B1 * | 4/2001 | Black et al. | 607/122 |
| 6,370,434 B1 * | 4/2002 | Zhang et al. | 607/122 |
| 6,505,082 B1 | 1/2003 | Scheiner et al. | 607/123 |
| 6,587,733 B1 | 7/2003 | Cross, Jr. et al. | |
| 6,620,118 B1 * | 9/2003 | Prosl et al. | 604/5.01 |
| 6,909,918 B2 | 6/2005 | Stypulkowski | |
| 7,099,718 B1 * | 8/2006 | Thacker et al. | 607/117 |
| 7,212,867 B2 | 5/2007 | Van Venroij et al. | |
| 7,359,755 B2 * | 4/2008 | Jones et al. | 607/117 |
| 7,437,197 B2 * | 10/2008 | Harris et al. | 607/115 |
| 2003/0004438 A1 * | 1/2003 | Berthonnaud et al. | 600/595 |

FOREIGN PATENT DOCUMENTS

WO     WO 02/45795 A2     6/2002

OTHER PUBLICATIONS

PCT, Invitation to Pay Additional Fees and Communication relating to the results of the Partial International Search, PCT/US2004/039425, 6 pages, Apr. 6, 2005.

* cited by examiner

*Primary Examiner* — Nicole F Lavert
(74) *Attorney, Agent, or Firm* — Craig Hoersten; Christopher S. L. Crawford; Peter R. Lando

(57) ABSTRACT

A lead, method of manufacturing same, and system for stimulation is provided. The lead includes an insulative member or layer that masks a portion of the electrode(s) to effectively generate a directional lead that focuses or directs the stimulation to desired location(s). In another embodiment, the lead further includes a marking system to allow a clinician to orient the directional lead, as desired, while the lead is within a body.

18 Claims, 6 Drawing Sheets

DIRECTIONAL STIMULATION LEAD AND ORIENTATION SYSTEM

CROSS-REFERENCE TO RELATED APPLICATION

This application claims benefit and priority (under 35 U.S.C. §119(e)) to prior U.S. provisional application Ser. No. 60/524,982 filed on Nov. 25, 2003, and which is incorporated herein by reference.

TECHNICAL FIELD OF THE INVENTION

The present invention relates to electrical leads, and in particular, an electrical lead for use in the medical field. [The present invention relates to electrical leads, percutaneous needles and methods of implanting such leads]

BACKGROUND

Implantable leads having electrodes are used in a variety of applications, including the delivery of electrical stimulation to surrounding tissue, neural or otherwise, as well as measuring electrical energy produced by such tissue. Some leads include lumens for the delivery of other elements, including chemicals and drugs. Whether in a stimulation, sensing or element delivery capacity, such leads are commonly implanted along peripheral nerves, within the epidural or intrathecal space of the spinal column, and around the heart, brain, or other organs or tissue of a patient.

Differing techniques have been utilized to construct or manufacture such leads. Some prior art leads and methods of manufacture have been disclosed in several United States patents, such as U.S. Pat. Nos. 5,016,646 (Gotthardt, et al.), 5,433,742 (Willis), 6,208,881 (Champeau) and 6,216,045 (Black, et al.), which are each incorporated herein by reference. One example of a directional brain stimulation and recording leads is disclosed in PCT publication WO 02/045795 (Jun. 13, 2002), which is incorporated herein by reference. A length of tubing having a window cut therein forms a sleeve insulating member (or formed by injection molding, vulcanization molding) that is placed over the distal end of the lead.

Generally, several elements (conductors, electrodes and insulation) are combined to produce a lead body. A lead typically includes one or more conductors extending the length of the lead body from a distal end to a proximal end of the lead. The conductors electrically connect one or more electrodes at the distal end to one or more connectors at the proximal end of the lead. The electrodes are designed to form an electrical connection or stimulus point with tissue or organs. Lead connectors (sometimes referred to as contacts, or contact electrodes) are adapted to electrically and mechanically connect leads to implantable pulse generators or RF receivers (stimulation sources), or other medical devices. An insulating material typically forms the lead body and surrounds the conductors for electrical isolation between the conductors and protection from the external contact and compatibility with a body.

Such leads are typically implanted into a body at an insertion site and extend from the implant site to the stimulation site (area of placement of the electrodes). The implant site is typically a subcutaneous pocket that receives and houses the pulse generator or receiver (providing a stimulation source). The implant site is usually positioned a distance away from the stimulation site, such as near the buttocks or other place in the torso area. In some cases, the implant site (and/or insertion site) is located in the lower back area, and the lead may extend through the epidural space (or other space) in the spine to the stimulation site (middle or upper back, or neck or brain areas). In other cases, the implant site may be located in the brain or other part of the body. In still other cases, the stimulation source may not be implanted, and may be external to the body.

Application of specific electrical fields to spinal nerve roots, spinal cord, deep brain stimulation, and other nerve bundles or tissue for the purpose of pain control has been actively practiced for years. While a precise understanding of the interaction between the applied electrical energy and the stimulated tissue is not fully appreciated, it is known that application of an electrical field to spinal or other tissue (e.g., spinal nerve roots and spinal cord bundles) can effectively mask certain types of pain transmitted from regions of the body associated with the stimulated tissue.

It is known that each exterior region, or each dermatome, of the human body is associated with a particular spinal nerve root at a particular longitudinal spinal position. The head and neck regions are associated with C2-C8, the back regions with C2-S3, the central diaphragm is associated with spinal nerve roots between C3 and C5, the upper extremities correspond to C5 and T1, the thoracic wall extends from T1 to T11, the peripheral diaphragm is between T6 and T11, the abdominal wall is associated with T6-L1, the lower extremities related to L2 to S2, and the perineum from L4 to S4. By example, to address pain sensations that commonly focus on the lower back and lower extremities, a specific energy field can usually be applied to a region between bony level T8 to T10. As should be understood, successful therapy management and the avoidance of stimulation in unafflicted regions generally requires the applied electric field to be properly positioned longitudinally along the dorsal column.

Therapy-managing electrical energy is commonly delivered through electrodes positioned at the desired stimulation site. The electrodes are generally carried by one of two types of leads: percutaneous and laminotomy (commonly referred to as "paddle" leads).

Percutaneous leads (including catheter types) are generally small in diameter and have a plurality of spaced electrodes. Percutaneous leads are typically placed within the body through the use of a Touhy-like needle. For insertion, the Touhy-like needle is passed through the skin at the desired location (insertion site) and the lead is inserted through the needle.

Laminotomy leads have a paddle configuration, and are generally larger than percutaneous leads, and typically possess a plurality of electrodes (for example, two, four, eight, or sixteen) arranged in one or more columns.

Laminotomy leads are generally used for applications in which is it desirous that the applied electrical energy (stimulation) be directional in nature, such as to address both unilateral and bilateral pain, where electrical energy may be administered using either column independently (on either side of the midline) or administered using both columns to create an electric field which traverses the midline. A multi-column laminotomy lead may enable reliable positioning of a plurality of electrodes, and in particular, provide a plurality of electrode columns that do not readily deviate from an initial implantation position/orientation.

However, laminotomy leads require a significant surgical procedure for implantation. The surgical procedure generally requires the resection and removal of certain tissue (vertebral tissue in the case of spinal applications) to allow both access to the dura and proper positioning of a laminotomy lead.

Percutaneous leads, in contrast, require a less-invasive implantation method, and with a plurality of electrodes, provide a user the ability to create almost any electrode array. However, prior art percutaneous leads generally have band-type electrodes whereby the electrical energy field radiates circumferentially and therefore the electrical energy may not be focused solely on the desired area. Although likely more stable during use and directional in nature, laminotomy leads require a more complicated surgical procedure for implantation and removal.

Notwithstanding the range of electric fields that are possible with conventional stimulation leads, in certain instances it is necessary to concentrate electrical energy at a particular point, or over a small region. As an example of such occasion, assume therapy-managing electrical energy is applied at or about T8 to address only localized lower back pain. At T8, spinal nervous tissue corresponding to the patient's lower extremities may also commingle with the specific spinal nervous tissue associated with the lower back. Since it is common that the lower back-related spinal nervous tissue is deeply embedded within the combined spinal nervous tissue, it becomes desirable to focus applied electrical energy to the targeted nervous tissue to (i) reach the deeply situated target nervous tissue and (ii) avoid undesirable stimulation of unafflicted regions, while avoiding surgical procedures for the lead(s) implantation and removal.

Accordingly, a need exists for a stimulation lead that includes a structural arrangement that facilitates directional concentration of delivered electrical energy at a point, i.e., for a given electrode, or over a small region, i.e., for a plurality of electrodes, and at the same time, may be implanted (and/or removed) without significant surgical procedure.

Additionally, implantation of leads using percutaneous methods involves the insertion of the lead into the body via a needle used as a passageway into the body. During the insertion procedure, the lead is pushed (forward) into the body, and in some occasions, there is a need for the lead to be pulled back (partly or completely) through the needle. This problem is described further by reference to FIG. 10. FIG. 10 illustrates the lead or catheter being inserted through the needle, and the potential problem when the lead is pulled back through the needle, likely due to repositioning by the clinician. When this occurs with prior art needles, there is a likelihood that the needle will cut or damage the lead, as shown.

Accordingly, there exists a need for a needle for use in percutaneous insertions which reduces the likelihood that, when an inserted lead is pulled back through the needle, the lead could be damaged.

SUMMARY

In accordance with one embodiment of the present invention, there is provided a lead having a lead body having a proximal end and a distal end. A connector is positioned proximate the proximal end while an electrode is positioned proximate the distal end. An insulative member is positioned over the electrode and includes an opening therethrough to expose at least a portion of the electrode. The lead further includes either a marker positioned proximate the distal end, or a marking system (or means for) providing a mechanism, for determining the orientation of the lead when the lead is implanted in a body.

In accordance with another embodiment of the present invention, there is provided a system for stimulating a portion of a body. The system includes a source for generating a stimulus and an implantable lead for receiving the stimulus from the source. The lead includes a lead body having a proximal end and a distal end. A connector is positioned proximate the proximal end while an electrode positioned proximate the distal end. An insulative member is positioned over the electrode and includes an opening therethrough to expose at least a portion of the electrode. The lead further includes a marking system (or means for) providing a mechanism for determining the orientation of the lead when the lead is implanted in a body.

In accordance with one yet another embodiment of the present invention, there is provided a lead having a lead body having a proximal end and a distal end. A connector is positioned proximate the proximal end while an electrode is positioned proximate the distal end. An insulative member is positioned over the electrode and includes an opening therethrough to expose at least a portion of the electrode, wherein the insulative member is substantially coextensive with the lead body such that an outer diameter of the lead body is substantially the same as an outer diameter of the insulative member.

In accordance with still another embodiment of the present invention, there is provided a system for stimulating a portion of a body. The system includes a source for generating a stimulus and an implantable lead for receiving the stimulus from the source. The lead includes a lead body having a proximal end and a distal end. A connector is positioned proximate the proximal end while an electrode positioned proximate the distal end. An insulative member is positioned over the electrode and includes an opening therethrough to expose at least a portion of the electrode, wherein the insulative member is substantially coextensive with the lead body such that an outer diameter of the lead body is substantially the same as an outer diameter of the insulative member.

In another embodiment, there is provided a method of manufacturing a lead. The method includes providing a lead body having a proximal end and a distal end having an electrode, forming an insulative layer over the electrode, and forming an opening through the insulative layer to expose at least a portion of the electrode.

In yet another embodiment, there is provided a method of manufacturing a lead. The method includes providing a lead body having a first diameter, a proximal end, a distal end, and a first insulative layer extending at least substantially the length of the distal end. A portion of the first insulative layer is removed at the distal end thereby leaving a remaining insulative layer, whereby the distal end of the lead body has a second diameter less than the first diameter. An electrode is place on the remaining insulative layer at the distal end and a second insulative layer is formed over the electrode to form the distal end having a diameter substantially equal to the first diameter. An opening is formed through the second insulative layer to expose at least a portion of the electrode.

BRIEF DESCRIPTION OF THE DRAWINGS

For a more complete understanding of the present invention, and the advantages thereof, reference is now made to the following descriptions taken in conjunction with the accompanying drawings, wherein like numbers designate like objects, and in which.

DETAILED DESCRIPTION OF THE INVENTION

Figure 1:
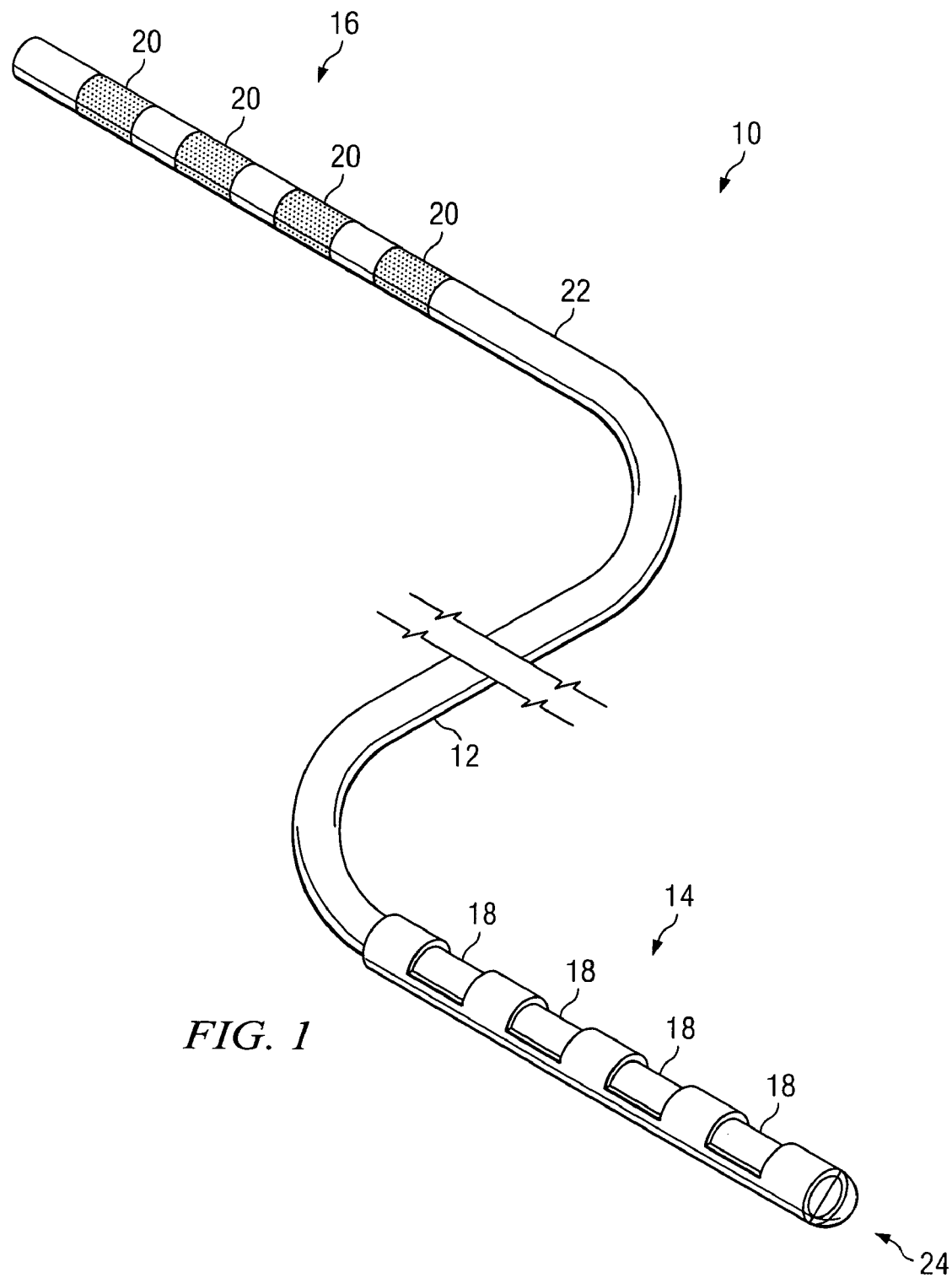
FIG. 1 is perspective view of a lead in accordance with the present invention.
Figure 12:
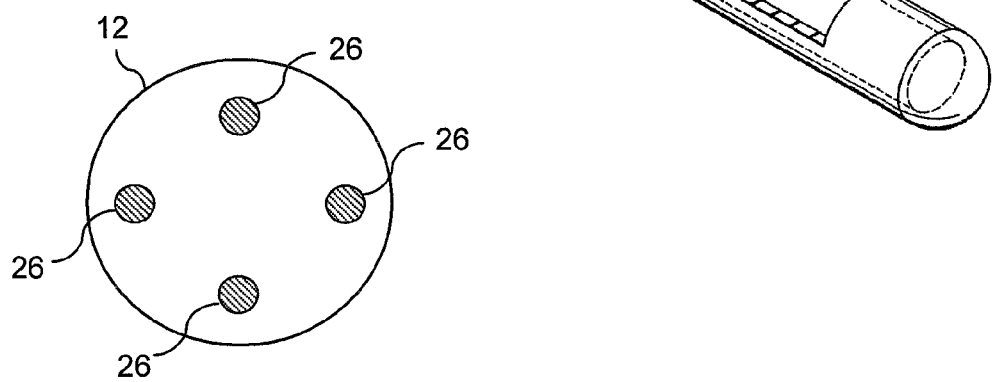
FIG. 12 depicts a cross-sectional view of a lead body with a plurality of conductors that may be used to implement some embodiments.

With reference to FIG. 1, there is illustrated an embodiment of a lead 10 in accordance with the present invention. The lead 10 includes a distal end 14 and a proximal end 16. The lead 10 includes a lead body 12 that extends from the distal end 14 to the proximal end 16. The distal end 14 of the lead 10 is shown including four electrodes 18. The proximal end 16 of the lead 10 is shown including four contact electrodes (or ring electrodes) 20 that form a lead connector. The lead 10 generally includes one or more conductors 26 (shown in FIG. 12) extending a substantial portion of the lead 10 to electrically connect the contact electrodes 20 to respective electrodes 18. An optional lumen 24 is shown that extends through the lead 10 and may be used for different purposes, including the delivery of chemicals or drugs.

As will be appreciated, any number of conductors 26, electrodes 18 and contact electrodes 20 may be utilized, as desired. For purposes of illustration only, the lead 10 is shown with four contact electrodes 20 and four electrodes 18. It will be further understood that the distal end 14 of the lead 10 is shown with electrodes 18 as described further below. In addition, other types, configurations and shapes of contact electrodes 20 (and lead connectors) as known to those skilled in the art may be used, as desired.

Typically, the lead body 12 is a structure having a round cross-section. Alternatively, the cross-section of the lead body 12 may be configured in any number of cross-sectional shapes appropriate for the specific application. The figures and following description generally refer to a round cross-sectional shape for the lead body 12 for illustrative purposes only. The lead body 12 generally includes a lead body insulator 22 configured to insulate the conductors 26 and presents a biocompatible external surface to the body tissue. In one embodiment, the lead body insulator 22 is coextensive with the conductors 26.

The lead body insulator 22 is formed of insulating material typically selected based upon biocompatibility, biostability and durability for the particular application. The insulator material may be silicone, polyurethane, polyethylene, polyamide, polyvinylchloride, PTFT, EFTE, or other suitable materials known to those skilled in the art. Alloys or blends of these materials may also be formulated to control the relative flexibility, torqueability, and pushability of the lead 10. Depending on the particular application, the diameter of the lead body 12 may be any size, though a smaller size is more desirable for neurological and myocardial mapping/ablation leads and neuromodulation and stimulation leads.

The conductors (not shown) may take the form of solid wires, drawn-filled-tube (DFT), drawn-brazed-strand (DBS), stranded wires or cables, ribbons conductors, or other forms known or recognized to those skilled in the art. The composition of the conductors may include aluminum, stainless steel, MP35N, platinum, gold, silver, copper, vanadium, alloys, or other conductive materials or metals known to those of ordinary skill in the art. The number, size, and composition of the conductors will depend on the particular application for the lead 10, as well as the number of electrodes.

The conductors may be configured along the lead body 12 in a straight orientation or spirally or helically wound about the lumen 24 or center of the lead body 12. The conductors are typically insulated from the lumen 24, from each other, and from the external surface of the lead 10 by the insulative material 22. The insulative material 22 may be of a single composition, or multiple layers of the same or different materials.

At least one electrode 18 is positioned at the distal end 14 of the lead body 12 for electrically engaging a target tissue or organ. In addition, at least one connector 20 is positioned at the proximal end 16 of the lead body 12 for electrically connecting the conductors 26 to a stimulating or receiving source. In one embodiment, the lead 10 is generally configured to transmit an electric signal from an electrical source (see FIGS. 4 and 5) for application at, or proximate to, a spinal nerve or peripheral nerve, or other tissue.

The electrodes 18 and contact electrodes 20 are typically made of a conductive material such as platinum, gold, silver, platinum-iridium, stainless steel, MS35N, or other conductive materials, metals or alloys known to those skilled in the art. The size of the electrodes 18 is generally chosen based upon the desired application. The contact electrodes 20 generally have a size and configuration appropriate to connect the lead 10 to a desired electrical source or receiver.

Figure 2A:
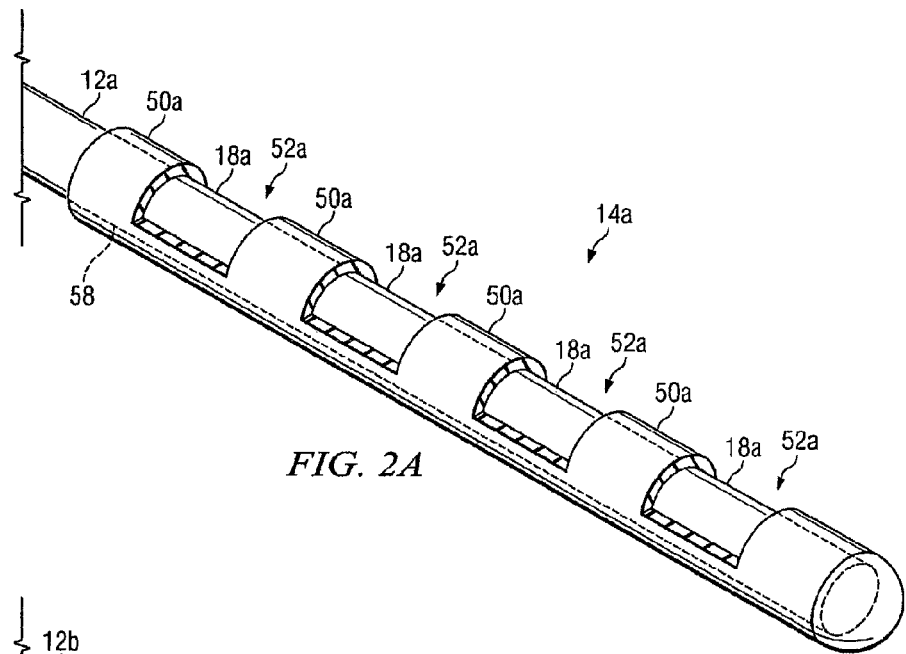
FIG. 2A is a more detailed perspective view of one embodiment of the distal end of the lead shown in FIG. 1.
Figure 2B:
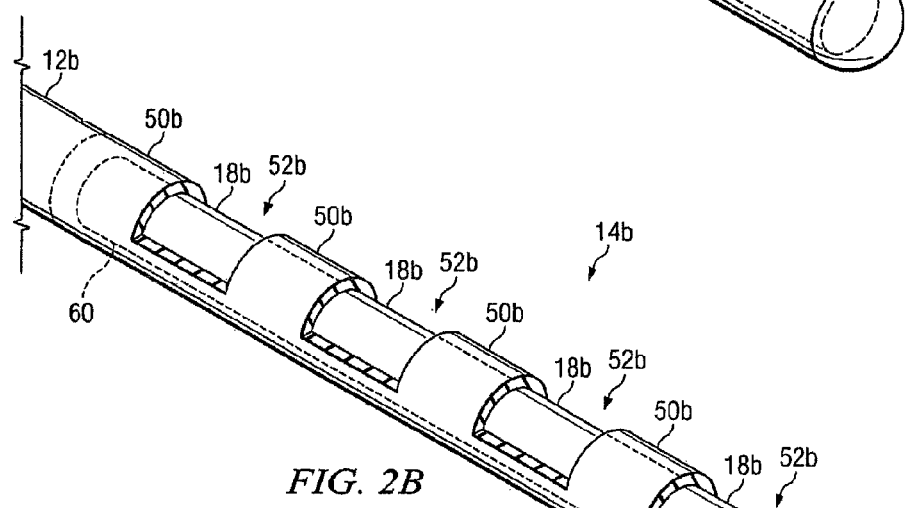
FIG. 2B is a more detailed perspective view of another embodiment of the distal end of the lead shown in FIG. 1.

With reference to FIGS. 2A and 2B, there are illustrated detailed perspective views of distal ends 14a, 14b of the lead 10 of the present invention. In FIG. 2A, the distal end 14a the lead body 12a is shown with an insulative member 50a (or insulating material) extending over the electrodes 18a. Openings 52a (i.e., windows, apertures) extending through the insulative member 50a are formed to expose at least a portion of the electrodes 18a. As will be appreciated, the dotted line identified by reference numeral 58 assists in illustrating the location of the lead body 12a in relation to the insulative member 50a. Methods of construction of the lead 10 having a distal end 14a, as shown in FIG. 2A, will be described in further detail below.

In FIG. 2B, the distal end 14b of the lead body 12b is shown with an insulative member 50b (or insulating material) extending over the electrodes 18b. Openings 52b (i.e., windows, aperatures) extending through the insulative member 50b are formed to expose at least a portion of the electrodes 18b. As will be appreciated, the dotted line identified by reference numeral 60 assists in illustrating the location of the lead body 12b in relation to the insulative member 50a. The construction of the lead 10 having a distal end 14b, as shown in FIG. 2B, will be described in further detail below.

With respect to both embodiments shown in FIGS. 2A and 2B, in one embodiment, the electrodes 18 are spaced apart and extend only substantially circumferentially around the lead body 12 (not shown) or only extend around a predetermined distance as desired (i.e. such as from about 45 degrees to about 180 degrees, or one-eighth to one-half the circumference). In another embodiment, the electrodes 18 extend completely around the lead body 12, as shown in FIGS. 2A and 2B, and are typically referred to as band electrodes. In addition, in one embodiment (as shown), each of the electrodes has a corresponding opening 52 through the insulative member 50. In another embodiment (not shown), the exposed portions of the electrodes 18 are exposed through the use of a single opening 52 in the insulative member 50, or any number of openings could be used each exposing one or multiple electrodes.

The location and shape of the openings 52 in the insulating member 50 mask a portion of the electrodes 18 and function to limit the electrical energy that is transmitted from each of the electrodes 18 when activated (stimulus) and/or to direct the energy in a desired direction. The energy from the electrodes 18 (or electrode array) can be focused in a limited direction less than the typical 360 degrees associated with band electrodes (a length along the circumference and longitudinal length may be desired, and in one embodiment, about 10 to 180 degrees of the circumference is possible, with about 45 or 90 degrees preferred).

As illustrated in FIGS. 2A and 2B, the openings 52 are substantially aligned parallel to the longitudinal axis of the lead body, and similar in size and shape, and thus produce a lead that is unidirectional. Other alignments, sizes and shapes of the openings may be used, for the specific application(s) as desired so that the lead has more than one "direction" of stimulation; the direction of stimulation depending on which electrode is used and the alignment of that electrode's opening. As will be appreciated, in another embodiment, an opening 52 may expose more than one of the electrodes 18.

As is known in the art, following implantation in the spinal area, tissue will grow around the electrode (paddle or percutaneous lead) and will usually increase the impedance associated with the electrode, thus reducing its ability to electrically couple with the targeted tissue. In order to maintain a constant or adequate degree of stimulation, it may be necessary to increase the energy delivered as the impedance increases. This creates the risk of stimulating or over-stimulating areas that are not intended to be stimulated. One typical solution to this problem has been to use a paddle lead, however, a paddle lead is large and is not percutaneously implanted, therefore requires significant surgical procedure and is guided to the target area. Additionally it is not appropriate in certain applications, such as for brain stimulation leads.

The directional or unidirectional lead 10 provided by the present invention is a percutaneous lead that directs the energy array of the electrode in a specified or desired direction. With this ability, a clinician can target a small area of nerves for stimulation without the danger of over-stimulation of non-targeted nerves or other nearby tissues.

The present invention provides a percutaneous lead capable of directionally sending energy from the lead. The directional capability of this lead is derived from the fact that part of the electrode(s) associated with the lead is masked by insulative material. Stimulation energy from the electrode array can be focused in a desired (and/or limited) direction (or specific area or point) that is less than 360 degrees (as measured circumferentially). The present invention lead has the same uses as traditional paddle leads, but may be smaller in size and shape. The directional lead is typically the same size and shape as a traditional percutaneous lead. With this in mind, it is possible to implant the lead using the same techniques used to implant traditional percutaneous leads via needle. Thus, the present invention lead provides a percutaneous lead having selective directional stimulation. As will be appreciated, use of two or more leads having a directional nature allow the electric fields to be directed between the two leads to more effectively stimulate the targeted tissue while avoiding excess stimulation of other structures.

With regards to the embodiments shown in FIGS. 2A and 2B, the insulative members 50*a*, 50*b* may be formed from a variety of materials including biocompatible plastics and other suitable insulative materials, such as polyurethane, pellethane, or the like. In one embodiment, the insulative members 50*a*, 50*b* are a separate and sleeve-like member that is placed over the distal end of the lead. The windows 52*a*, 52*b* may be formed, cut or machined within a length of tubing to form the insulating members 50*a*, 50*b*. Also, the insulating members 50*a*, 50*b* may be formed by any suitable molding technique, such as injection molding or the like. After the insulative members 50*a*, 50*b* are prepared or provided, the member is placed/applied/fixed (not shown, and by various methods known to those skilled in the art) over the distal end to cover a portion of the electrode(s) and expose a portion of the electrode(s).

Figure 3A:
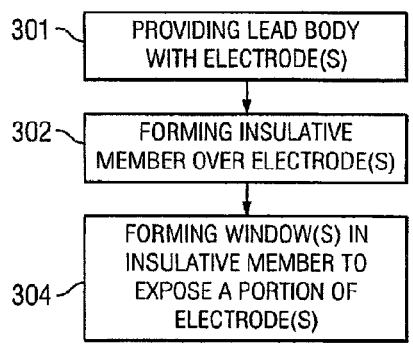
FIG. 3A illustrates one embodiment of a process of making the lead shown in FIG. 2A.
Figure 3B:
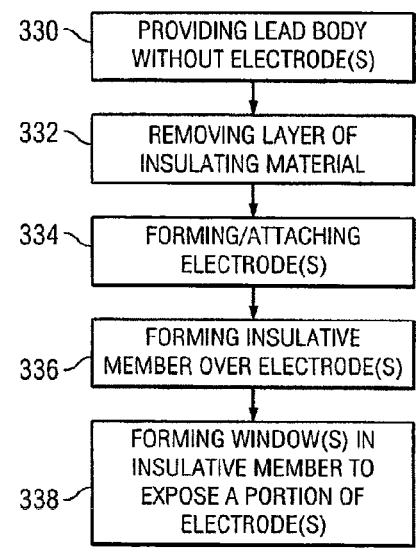
FIG. 3B illustrates one embodiment of a process of making the lead shown in FIG. 2B.

With reference to FIGS. 3A and 3B, there are shown embodiments of additional processes or methods for manufacturing the lead 10 of the present invention. With reference to FIG. 3A, at a step 301, a typical lead body is provided. The lead body 12*a* may be a lead body constructed according to methods and processes generally available or known to those skilled in the art, such as those described in U.S. Pat. No. 6,216,045, which is incorporated herein by reference. At a step 302, the insulating member or insulating layer 50*a* is formed over the electrodes 18*a* (see FIG. 2A). At a step 304, the openings 52*a* (apertures or windows) are formed to expose at least a portion of the electrodes 18*a*. In the embodiment shown, the insulating member 50*a* is formed over the distal end 14 of the lead 10. Alternatively, the insulating member 50*a* may be formed over a substantial length of the lead 10, and may extend from the distal end 14 to a point at or near the proximal end 16. In one embodiment, the insulative member 50*a* and windows 52*a* are formed as described previously.

With reference to FIG. 3B, at a step 330, a typical lead body is provided prior to affixation or placement of the electrodes 18*b*. The lead body 12*b* may be a lead body constructed according to methods and processes generally available or known to those skilled in the art, such as those described in U.S. Pat. No. 6,216,045. At a step 332, a layer of the existing lead body insulator 22 is removed along the distal end 14 (see dotted line identified by reference numeral 60 in FIG. 2B illustrating the removal of the existing layer). This may be accomplished by etching, grinding, or other techniques known to those skilled in the art. At a step 334, the electrodes 18*b* are attached (and electrically connected to the conductors, not shown) in known fashion.

At a step 336, the insulating member or insulating layer 50*b* is formed over the electrodes 18*b* (see FIG. 2B). At a step 338, the openings 52*b* (apertures or windows) are formed to expose at least a portion of the electrodes 18*b*. In the embodiment shown, the insulating member 50*b* is formed over the distal end 14 of the lead 10 (alternatively, the insulating member 50*b* may be formed over a substantial length of the lead 10, and may extend from the distal end 14 to a point at or near the proximal end 16). In one embodiment, the insulative member 50*b* and windows 52*b* are formed as described previously.

Alternatively, the lead of step 330 may include the electrodes, and the removing step 332 may further include removing a layer of the insulative material and a similar outer layer of the electrode(s). In this embodiment, the step 334 would be omitted.

In one embodiment, the insulating member or layer 50a, 50b is made of any suitable insulative material sufficient to substantially prevent or substantially reduce electrical radiation from the electrodes 18a, 18b. In another embodiment, the insulating member or layer 50a, 50b is composed of paralyne. Thicknesses of the insulating member or layer 50a, 50b can range from 0.0005 to 0.002 inches, and is preferable in the range of 0.0005 to 0.0009 inches, and may be about 0.0007 inches. The insulative member or layer 50a, 50b may be formed in the forming step 302, 336 by various methods, including chemical or physical vapor deposition, sputtering, thermal growth, etc.

In one embodiment, the insulating member or layer 50a, 50b is formed over the entire portion of each electrode 18a, 18b and, subsequently, a selected portion (the portion desired to be exposed) of the insulating member 50a, 50b is removed to form the openings 52a, 52b. Different techniques may be utilized to form the openings 52a, 52b, including laser ablation, etching, cutting, or similar and like methods sufficient to remove a selected portion and expose the electrode 18a, 18b. In another embodiment, masking material (or a masking layer) (not shown) is used to selectively mask the portion of the electrode 18a, 18b desired to be exposed. The insulating member/layer 50a, 50b is formed on the distal end 14, and the masking material/layer is removed to expose the electrode 18a, 18b.

Additionally, the insulating member or layer 50 may be applied by insert-molding, coating followed by etching, scribing or cutting to define the windows 52a and 52b, or selective vapor deposition of insulative materials to form a patterned layer that defines one or more windows 52a and 52b.

In the embodiment shown in FIG. 2B (and steps described in FIG. 3B and above), the insulating member or layer 52a is substantially level or coextensive with the outer diameter of the remaining length of the lead body 12b. A step is formed at the distal end 14 to allow formation of the insulating member or layer 52a to be coextensive with lead body 12a, and wherein the outer diameter of the distal end 14 is substantially the same as the outer diameter of the lead body 12a.

Figure 6:
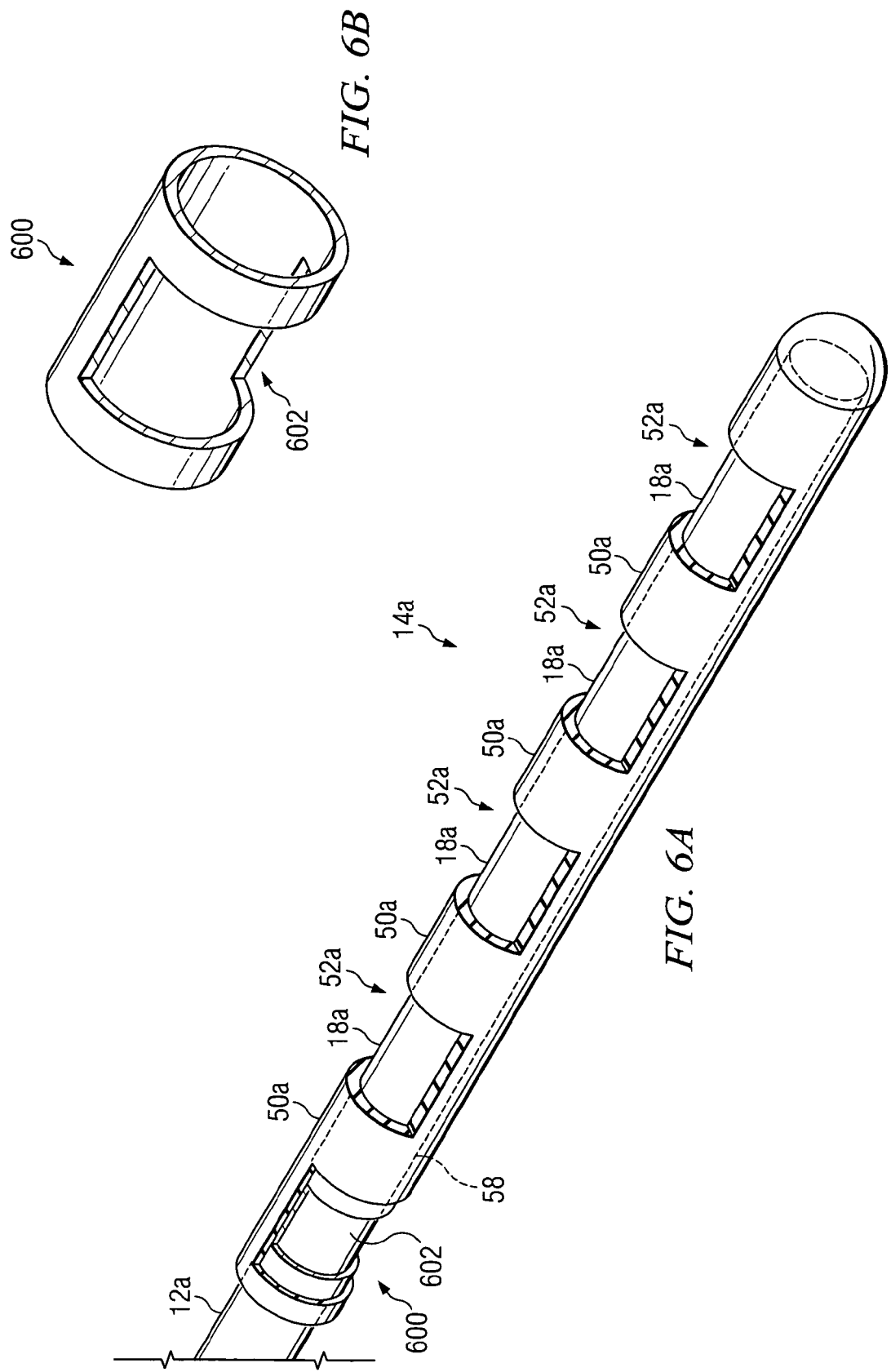
FIG. 6A shows the lead of FIG. 2A with one embodiment of the marking or orientation system.
FIG. 6B is an enlarged perspective view of the marker shown in FIG. 6A.

With reference to FIGS. 6A and 6B, the lead 10 of the present invention may incorporate a marking or orientation system, which provides a mechanism to orient the directional lead 10 while the lead is implanted in the body. Such orientation is desired to orient the lead to take advantage of the directional nature of the electrodes to target a desired area.

As shown in FIG. 6A, the marking system includes a marker (or marking band) 600. The marker 600 is positioned at a first location and affixed or attached to, or integrated with, the lead 10. In the embodiment shown, the marker 600 includes an electrode (or electrode-type) band (similar to electrodes 18) with a notch 602. The marker 600 is constructed of radio-opaque material that provides a marker, which is visible through the body when using a fluoroscope or X-ray device, or other similar or like devices, while the lead is within a body. The radio-opaque material may be a composition of platinum-iridium, or some other conductive or metallic material. The notch 602 depicted is an opening or window in the marker 600 where no radio-opaque material exists. As will be understood, the marker 600 may be integrated within the lead 10 during construction of the lead, in the methods as described above, or may be affixed, constructed or attached through additional steps.

The marker 600 is tubular in shape and resembles a band electrode. The notch 602 of the marker 600 typically extends circumferentially with the lead body for a predetermined distance or arc. In the embodiment shown, the notch 602 extends arcuately for a length equal to about 180 degrees (about one-half way around), or a 180 degree arc. In other embodiments, any length/arc may be chosen sufficient to provide the functionality described herein, including ranging from 90 degrees to 270 degrees or forty-five degrees. Moreover, the axial length of the marker 600 may be any desired length sufficient to obtain the desired results, but is typically about the same or shorter than axial length of the electrodes 18.

To function effectively as a marking or orientation system for orienting/positioning the lead within a body for directional stimulation, the notch (or the portion "non-visible" via fluoroscopy or X-ray) 602 of the marker 600 is oriented or fixed in a predetermined relation with respect to the exposed portions of the electrodes 18. As will be appreciated, depending on the shape and directional orientation of the electrodes 18 (exposed portions) and the marker 600, the marker 600 and electrodes 18 are fixed generally at a circumferential distance from each other. In the example illustrated in FIG. 6A, the marker 600 is positioned about ninety degrees offset from the electrodes 18. Knowledge of the fixed position of the marker 600 relative to the electrodes 18 and window 52 provides a marking or orientation system operable to allow a practitioner implanting the directional lead within a body to place the lead and orient the windows contained on the lead at the desired location and with the desired directional orientation.

While any offset positioning may be used, it appears that an offset of ninety degrees (plus or minus) may be more effective, as it is easier to view and comprehend such relative positioning with respect to two components.

Now with reference to FIG. 6B, there is illustrated an enlarged perspective view of the marker 600 showing the notch 602. The marker has a similar configuration as the band electrode with a section or portion (602) removed.

Those of ordinary skill in the art will readily understand that, when the lead with the marker 600 of the present invention is implanted, the marker silhouette viewable through utilization of a detecting device (e.g., fluoroscope or X-ray device) will show different configurations depending on the orientation of the lead. For example, assuming the notch size is approximately one-half the band, when the notch is facing directly toward or away from the detecting device, a complete band will be visible. Similarly, if facing directly perpendicular to the detecting device, the visible configuration will provide information as to the orientation of the lead (i.e. a C-shape). Therefore, the marker 600 will allow a clinician the ability to orient the lead in a fashion so as to direct the stimulation in a desired direction (using the directional electrodes).

The marker 600 is capable of recognition in the body through the use of a fluoroscope, radiation, or other similar or like technology. This allows a medical professional to determine the orientation of the directional electrodes of the lead relative to the targeted tissue. The marker(s) band within the lead allows a medical professional to quickly and easily determine the relative position of the electrode(s) 18a, 18b within lead 10 (see FIGS. 2A, 2B).

As will be appreciated, more than one marker 600 (not shown) may be optionally utilized. Further, the sizes, shapes and configurations of the marker 600 and the notch 602 may vary. While the embodiment of the marker 600 in FIGS. 6A and 6B is configured with a notch, another configuration may include only a single arc section of material (in the form of a semi-circle, without portions that extend completely about the lead). Another configuration (not shown) includes two diametrically opposed notches or holes in the marker material. In this way, orientation of the marker can be determined due to the alignment of the notches, which will become visible when substantially aligned.

It will be understood by those skilled in the art that the marking or orientation system may include a single marker, or multiple markers, each of the marker(s) having some recognition attribute (recognizable by some means). Such recognition attributes include radio-opaque or radiopaic and structural (e.g., notch or groove), and the system may utilize multiple markers each utilizing a different attribute to create a marking system for orienting the implanted lead (or simply for determining the orientation).

One characteristic of the embodiment shown in FIG. 2B (and in FIG. 2A when the insulating member 50a extends substantially the length of the lead 10) is that during lead insertion (via a needle), there are times when the lead may be pulled back through the needle. In such case, having an insulating member or layer that has an outer diameter greater than the overall diameter of the lead body, may result in undesirable cutting (damage) or catching of the lead by the edge of the needle as it is removed (in order to re-insert or reposition the lead through the needle).

However, even with leads having substantially the same outer diameter, prior art percutaneous insertion leads will tend to cut or damage a lead when it is pulled back through the needle.

Figure 7:
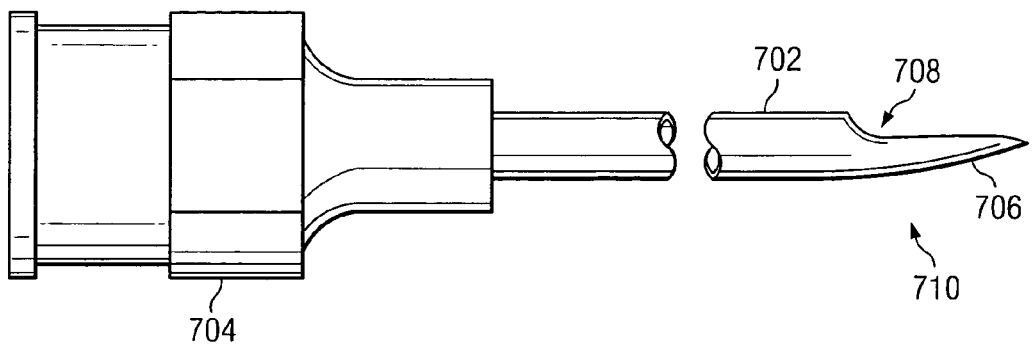
FIG. 7 illustrates a typical prior art percutaneous insertion needle.

Now with reference to FIG. 7, there is illustrated a typical prior art percutaneous insertion needle 700. The needle 700 includes a needle body 702 (with a lumen therethrough), a proximate end 704 (providing for insertion of a lead/catheter and/or stylet or other inserted device), a distal end 710, an introducer portion 706 with a slight curvature, and an orifice 708. Examples of such needles are epidural, Touhy and modified Touhy needles. The functionality and structure of these devices is well known to those skilled in the art and, therefore, no further description will be provided herein.

Figure 8:
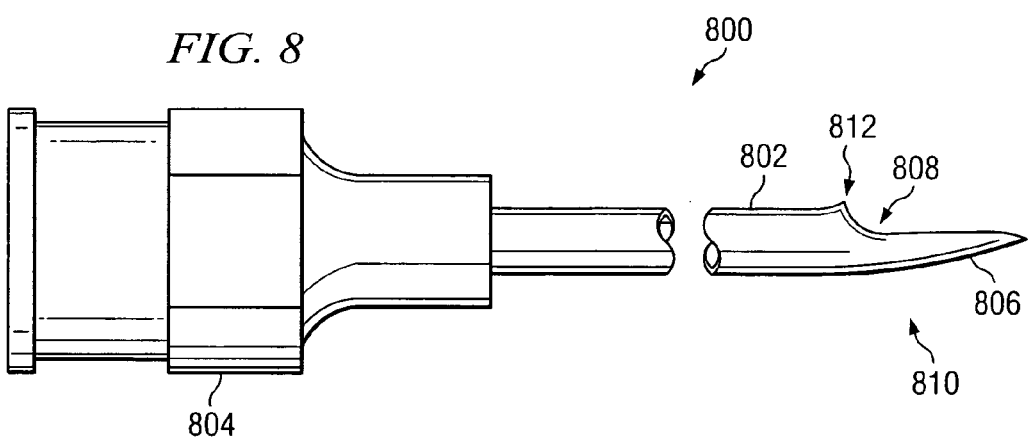
FIG. 8 illustrates a percutaneous insertion needle in accordance with the present invention.

With reference to FIG. 8, there is shown a needle 800 in accordance with the present invention. The needle 800 includes a needle body 802 (with a lumen therethrough), a proximate end 804 (providing for insertion of a lead/catheter and/or stylet or other inserted device), a distal end 810, an introducer portion 806 with a slight curvature, and an orifice 808. The needle 800 further includes a lip or flare 812 positioned proximate the heel edge of the orifice 808 of the needle 800. As used herein, the term "lead" includes catheters or other electrical or drug delivery devices typically inserted percutaneously through the needle.

Figure 9A:
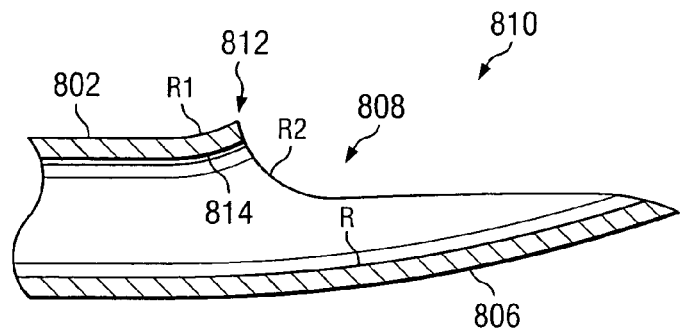
FIG. 9A is a partial side view showing the tip of the needle of FIG. 8.
Figure 9B:
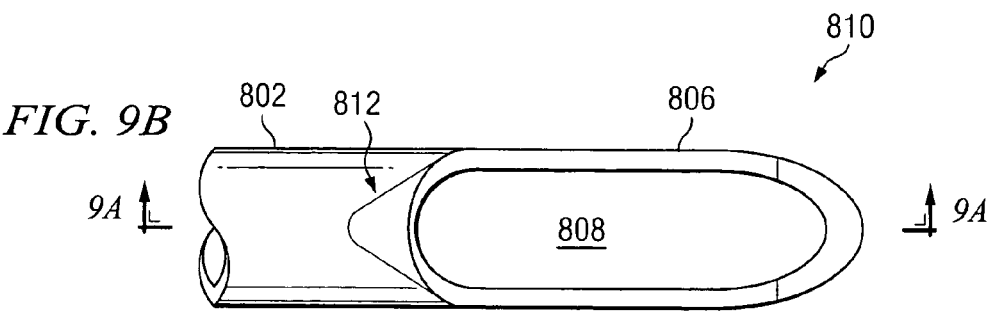
FIG. 9B is a partial top view showing the tip of the needle of FIG. 8.
Figure 10:
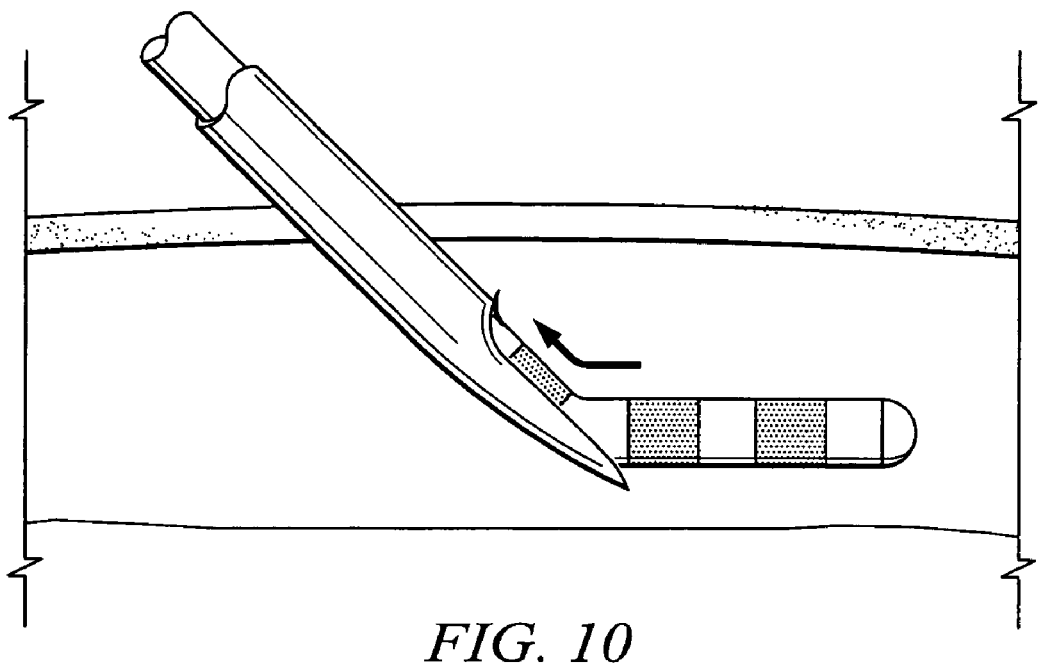
FIG. 10 illustrates a typical prior art needle and a problem associated therewith.
Figure 11:
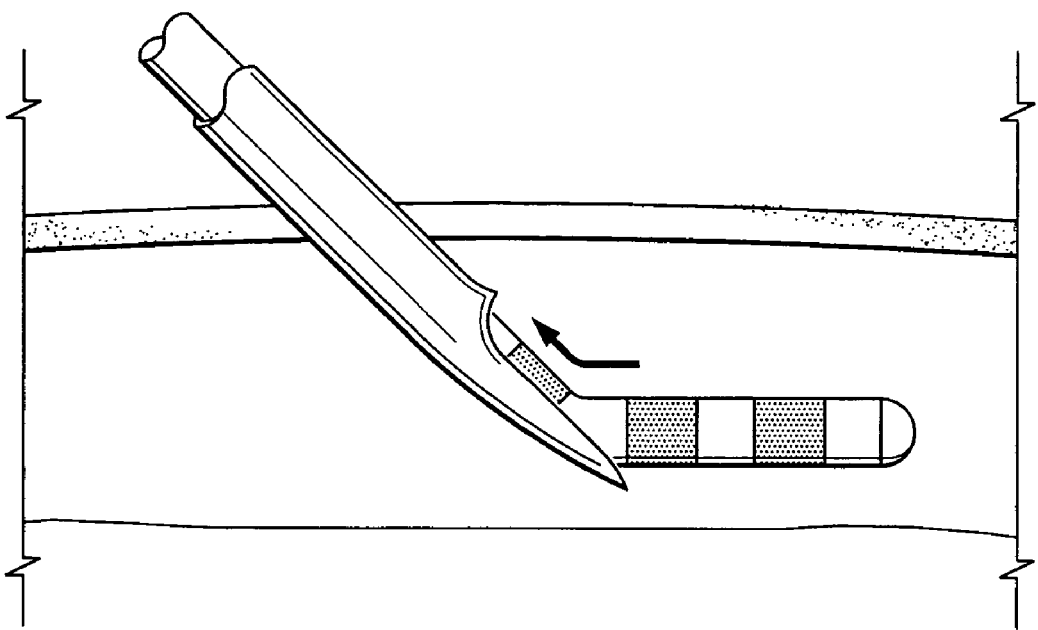
FIG. 11 illustrates the needle of the present invention showing a lead being pulled back through the needle and not being damaged.

Now referring to FIGS. 9A and 9B, there is illustrated a partial side view and partial tip view, respectively, showing the distal end tip portion of the needle of FIG. 8. The radius of curvature R for the introducer portion 806 is about 1 inch (in another embodiment is less than about 2 inches), and those skilled in the art will understand that other curvatures may be implemented. The lip or flare section 812 on a heel portion 814 of the orifice 808 includes a slight curvature. In one embodiment, the radius of curvature R1 of the section 812 is less than the radius of curvature R for the introducer portion 806. In another embodiment, the radius of curvature R1 is approximately 0.1 inches or less. This provides for the raised lip or flare at 812 that provides for a "funneling" or "channeling" location within the needle, as shown more fully in FIG. 11, to help guide the lead back into the needle in a manner such that the lead will not score or cut on the lip or flare (heel portion) if the lead is pulled back through the needle. The cross-section area at the lip portion is greater than the cross-section area at an adjacent body portion (towards the proximate end of the needle), or as differently described, the inner diameter of the needle at the lip portion is greater than the inner diameter of the needle at an adjacent body portion (towards the proximate end of the needle).

As described above, the configuration of the heel edge of the needle 800 as shown by the lip or flare section 812 helps reduces the likelihood that a lead/catheter inserted through the needle 800 (extending through the orifice 808) will become cut or damaged in the event the lead/catheter is pulled back through the needle toward the proximal end of the needle.

An orifice edge of the introducer section 808 further includes a radius of curvature R2 of approximately 0.05 inches.

FIG. 8 illustrates one embodiment of the needle 800 usable to insert and place any of the above-described inventive leads, or any prior art leads. The needle 800 defines an interior path that ultimately receives and guides a lead into an epidural space or other desired location within a body. Typically, both the needle 800 and stylet (not shown) are used in combination to facilitate penetration through human tissue to the desired location.

In one embodiment of an implantable procedure, a small incision is first made in a body using a scalpel at the desired site of insertion. Making an initial incision prevents the application of excess force to the tip of the needle 800 and further avoids the undesirable introduction of dermal matter into the location. The needle 800 is introduced through the incision at an angle that allows passage of the needle 800 between vertebral bodies. Once the distal end 810 of the needle 800 is positioned within and opens into the desired location (typically, epidural space), a lead is inserted.

Figure 4:
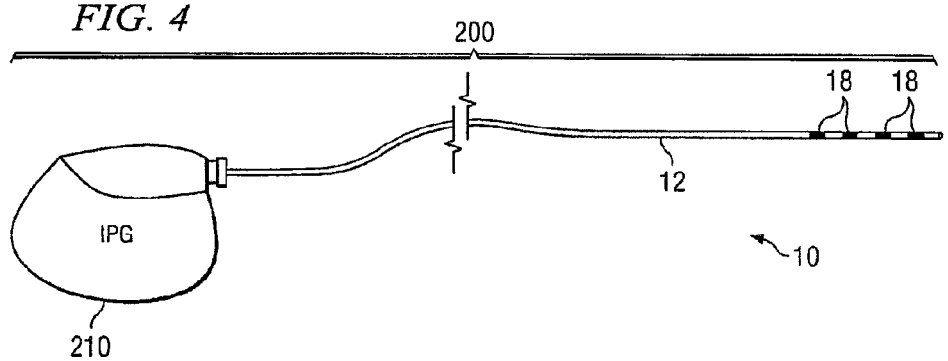
FIG. 4 illustrates one embodiment of a system for stimulation in accordance with the present invention.
Figure 5:
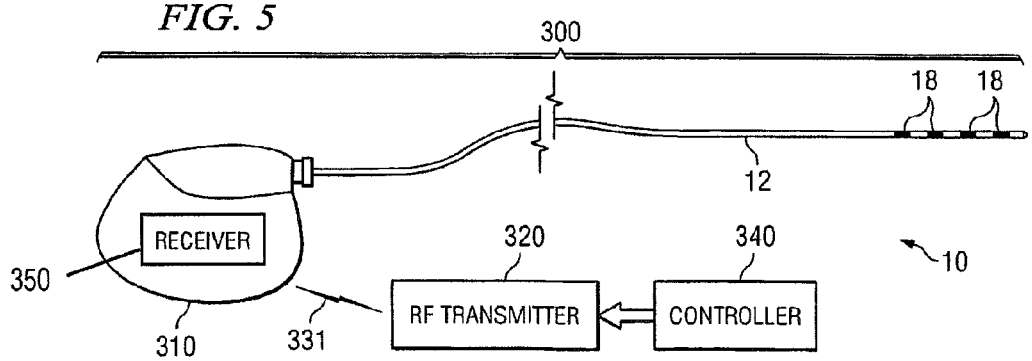
FIG. 5 illustrates another embodiment of a system for stimulation in accordance with the present invention.

Now referring to FIGS. 4 and 5, there are shown two embodiments of a stimulation system 200, 300 in accordance with the present invention. The stimulation systems generate and apply a stimulus to a tissue or to a certain location of a body. In general terms, the system 200, 300 includes a stimulation or energy source 210, 310 and a lead 10 for application of the stimulus. The lead 10 shown in FIGS. 4 and 5 is the lead 10 of the present invention.

As shown in FIG. 4, the stimulation system 200 includes the lead 10 that is coupled to the stimulation source 210. In one embodiment, the stimulation source 210 includes an implantable pulse generator (IPG). As is known in the art, an implantable pulse generator (IPG) is capable of being implanted within the body (not shown) that is to receive electrical stimulation from the stimulation source 210. An exemplary IPG may be one manufactured by Advanced Neuromodulation Systems, Inc., such as the GENESIS® System, part numbers 3604, 3608, 3609, and 3644.

As shown in FIG. 5, the stimulation system 300 includes the lead 10 that is coupled to the stimulation source 310. The stimulation source 310 includes a wireless receiver (not shown). The stimulation source 310 may also be referred to as a wireless receiver. As is known in the art, the stimulation source 310 comprising a wireless receiver is capable of being implanted within the body (not shown) that is to receive electrical stimulation from the wireless receiver 310. An exemplary wireless receiver 310 may be those receivers manufactured by Advanced Neuromodulation Systems, Inc., such as the RENEW® System, part numbers 3408 and 3416.

The wireless receiver 350 within stimulation source 310 is capable of receiving wireless signals from a wireless transmitter 320. The wireless signals are represented in FIG. 5 by wireless link symbol 331. The wireless transmitter 320 and a controller 340 are located outside of the body that is to receive electrical stimulation from the stimulation source 310. A user of the stimulation source 310 may use the controller 340 to provide control signals for the operation of the stimulation source 310. The controller 340 provides control signals to the wireless transmitter 320. The wireless transmitter 320 transmits the control signals (and power) to the receiver in the stimulation source 310, and the stimulation source 310 uses the control signals to vary the signal parameters of the electrical signals that are transmitted through lead 10 to the stimulation site. An exemplary wireless transmitter 320 may be those transmitters manufactured by Advanced Neuromodulation Systems, Inc., such as the RENEW® System, part numbers 3508 and 3516.

As will be appreciated, the contact electrodes 20 are not visible in FIG. 4 (or FIG. 5) because the contact electrodes 20 are situated within a receptacle (not shown) of the stimulation source 210, 310. The contact electrodes 20 are in electrical contact with a generator (not shown) of electrical signals within the stimulation source 210, 310. The stimulation source 210, 310 generates and sends electrical signals via the lead 10 to the electrodes 18. Understandably, the electrodes 18 are located at a stimulation site (not shown) within the body that is to receive electrical stimulation from the electrical signals. A stimulation site may be, for example, adjacent to one or more nerves in the central nervous system (e.g., spinal cord). The stimulation source 210, 310 is capable of controlling the electrical signals by varying signal parameters (e.g., intensity, duration, frequency) in response to control signals that are provided to the stimulation source 210, 310.

It may be advantageous to set forth definitions of certain words and phrases that may be used within this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and if the term "controller" is utilized herein, it means any device, system or part thereof that controls at least one operation, such a device may be implemented in hardware, firmware or software, or some combination of at least two of the same. It should be noted that the functionality associated with any particular controller may be centralized or distributed, whether locally or remotely.

Although the present invention and its advantages have been described in the foregoing detailed description and illustrated in the accompanying drawings, it will be understood by those skilled in the art that the invention is not limited to the embodiment(s) disclosed but is capable of numerous rearrangements, substitutions and modifications without departing from the spirit and scope of the invention as defined by the appended claims.

What is claimed is:

1. A stimulation lead for applying electrical pulses to tissue of a patient, comprising:
    a lead body of an insulative material;
    a plurality of conductors within the lead body;
    a plurality of terminals at a proximal end of the lead body for electrically coupling with a pulse generator;
    a plurality of electrodes at a distal end of the lead body for applying electrical pulses to tissue of the patient, each of the plurality of electrodes circumscribing the lead body;
    an insulative member disposed over the plurality of electrodes, the insulative member having a respective opening for each of the plurality of electrodes that only exposes a limited angular range of each electrode; and
    a marking structure for determining an angular orientation of the lead body, the marking structure disposed to at least partially circumscribe the lead body, wherein the marking structure comprises a radio-opaque portion such that an edge of the marking structure between the radio-opaque portion and a non-radio-opaque portion is substantially aligned with a mid-line of the exposed angular range of each electrode of the plurality of electrodes.

2. The stimulation lead of claim 1 wherein the non-radio-opaque portion of the marking structure is formed as a window in the marking structure.

3. The stimulation lead of claim 1 wherein the radio-opaque portion of the marking structure extends approximately 180° about the lead body.

4. The stimulation lead of claim 1 wherein the radio-opaque portion of the marking structure is formed of a metal material.

5. The stimulation lead of claim 1 wherein the radio-opaque portion of the marking structure comprises a metal arc affixed to the lead body.

6. The stimulation lead of claim 1 further comprising:
    a second marking structure for determining an angular orientation of the lead body, the second marking structure disposed to at least partially circumscribe the lead body, the second marking structure comprising radio-opaque and non-radio-opaque portions.

7. The stimulation lead of claim 6 wherein the second marking structure is disposed in an opposing angular orientation relative to the other marking structure.

8. The stimulation lead of claim 1 wherein the insulative member is a parylene coating applied to the lead body and electrodes.

9. The stimulation lead of claim 1 wherein the insulative material is a sleeve placed over the lead body.

10. A method of fabricating a stimulation lead for applying electrical pulses to tissue of a patient, the method comprising:
    providing a lead body of an insulative material with a plurality of conductors within the lead body;
    providing a plurality of terminals at a proximal end of the lead body for electrically coupling with a pulse generator;
    providing a plurality of electrodes at a distal end of the lead body for applying electrical pulses to tissue of the patient, each of the plurality of electrodes circumscribing the lead body;
    providing an insulative member disposed over the plurality of electrodes, the insulative member having a respective opening for each of the plurality of electrodes that only exposes a limited angular range of each electrode; and
    providing a marking structure for determining an angular orientation of the lead body, the marking structure disposed to at least partially circumscribe the lead body, wherein the marking structure comprises a radio-opaque portion such that an edge of the marking structure between the radio-opaque portion and a non-radio-opaque portion is substantially aligned with a mid-line of the exposed angular range of each electrode of the plurality of electrodes.

11. The method of claim 10 wherein the non-radio-opaque portion of the marking structure is formed as a window in the marking structure.

12. The method of claim 10 wherein the radio-opaque portion of the marking structure extends approximately 180° about the lead body.

13. The method of claim 10 wherein the radio-opaque portion of the marking structure is formed of a metal material.

14. The method of claim 10 wherein the radio-opaque portion of the marking structure comprises a metal arc affixed to the lead body.

15. The method of claim 10 further comprising:

providing a second marking structure for determining an angular orientation of the lead body, the second marking structure disposed to at least partially circumscribe the lead body, the second marking structure comprising radio-opaque and non-radio-opaque portions.

16. The method of claim 15 wherein the second marking structure is disposed in an opposing angular orientation relative to the other marking structure.

17. The method of claim 10 wherein the insulative member is a parylene coating applied to the lead body and electrodes.

18. The method of claim 10 wherein the insulative material is a sleeve placed over the lead body.

* * * * *